Figure 1:
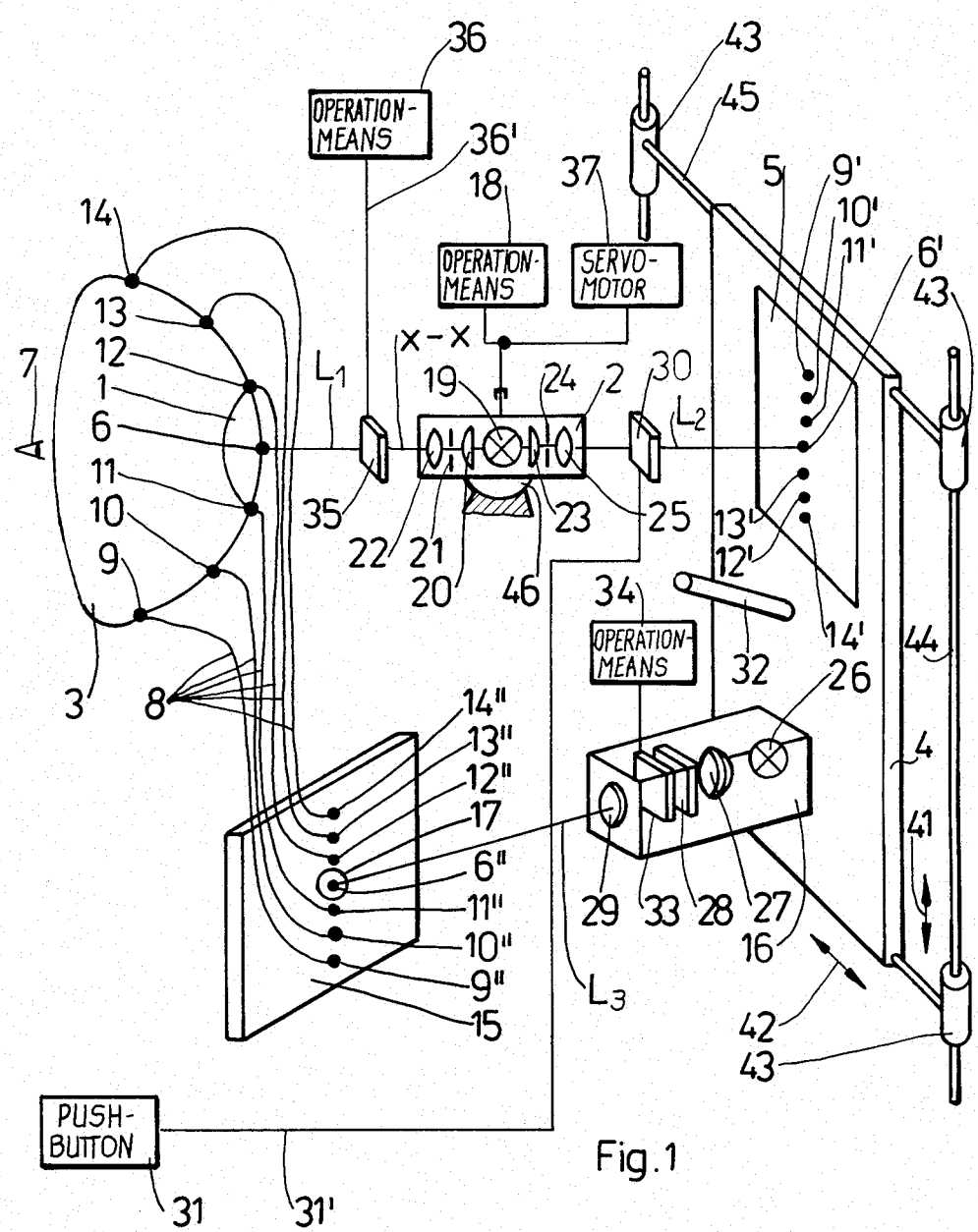

United States Patent [19]

Ludwig

[11] Patent Number: 4,490,023
[45] Date of Patent: Dec. 25, 1984

[54] ARRANGEMENT FOR TEST MARK POSITIONING IN SPHERIC PERIMETERS

[76] Inventor: Manfred Ludwig, 8, Pfälzer Strasse, Jena, District of Gera, German Democratic Rep.

[21] Appl. No.: 320,056

[22] Filed: Nov. 19, 1981

[30] Foreign Application Priority Data

Feb. 2, 1981 [DD] German Democratic Rep. ... 227363

[51] Int. Cl.$^3$ ............................................... A61B 3/02
[52] U.S. Cl. ..................................... 351/226; 351/224
[58] Field of Search ....................... 351/224, 225, 226

[56] References Cited

U.S. PATENT DOCUMENTS 4,059,348 11/1977 Jernigan ............................. 351/224

Primary Examiner—John K. Corbin
Assistant Examiner—Rodney B. Bovernick

[57] ABSTRACT

The invention relates to an arrangement for test mark positioning in spheric perimeters particularly for use in ophthalmological examinations. A semi-spherical perimeter screen has a central portion upon which a fixed mark is projected by a double projector the back-projection of which is indicated upon a visual field chart which permits recording of said back-projected fixed mark. A further projector connected to the displaceable visual field chart carrier produces discrete test marks via light cables around the central portion of said screen. Thus it is feasible to continuously detect the visual field of a patient's eye by cooperation between the patient's eye, the fixed mark and the discrete marks and by respective displacements of the projectors and hence the marks involved.

5 Claims, 2 Drawing Figures

ARRANGEMENT FOR TEST MARK POSITIONING IN SPHERIC PERIMETERS

The invention relates to an arrangement for test mark positioning and detection for determining the field of sight of a patient, particular for use in spheric perimeters.

The inventional arrangement permits application with all known perimetric methods.

Previous technical solutions can be subdivided into three types concerning the kind of test mark positioning and the positioning into a visual field scheme.

The DE Patent Specification No. 2356778 discloses a system for positioning a marking at any desired point of the visual field the direction of displacement of the marking being selectable at will.

In a second type, a marking is positioned at any desired point of the visual field.

The directions of movement are fixed and have meridians and parallels of latitude of the perimeter semisphere as axes relative to the direction of sight.

The G.D.R. Patent Specification No. 122779 discloses a third basic type where the markings are disposed on discrete points which are distributed about a semi-sphere. With the first basic type the marking is produced by a projector which is rotatable about two axes at right angles to the direction of projection.

The direction control is either performed electronically by a servo-motor or mechanically by a lever system. Since the perimeter axis does not extend into a patient's pupil the projector cannot be positioned in the center of the sphere.

Therefore the projector needs variable positioning so to entirely sweep a visual field. This involves considerable technical expenditures, both, with mechanic control and electronic control.

With the second basic type the projector is moved along the equatorial arc and is only tiltable about one axis. This solution is simple compared to the former one, it is, however, disadvantageous as to the limitations of the scotomata cannot always be scanned perpendicularly.

It is a further disadvantage of the first two type solutions that these do not permit random examinations.

The third solution type does without technically complicated and expensive mechanisms for position markings, but it only permits random examinations, the number of such examinations is considerably limited for practical reasons and the respective devices for performing such examinations already include a random examination program.

Central scotomata can be detected with the first two type solutions only be employing additional projectors, and the third type solution does not permit a detection at all.

All the previous solutions have the common disadvantage that the position of the test marking has to be determined relative to the direction of sight which is defined by the position of a fixed mark.

It is an object of the present invention to obviate the above disadvantages.

It is a further object of the present invention to provide an arrangement for test mark positioning in spheric perimeters which permits kinetic and static perimetric operation over the entire visual field, as well as random tests.

It is still a further object of the present invention to provide a device for test mark positioning which permits a selective switching of discrete test markings arranged upon a semi-sphere about a pole and detecting of said markings under use of an illuminated fixed point.

These and other objects are realised in an arrangement for test marking positioning and detecting which comprises a semi-spheric perimeter screen which has a central pole portion of translucent material.

A fixed point is projected to the center of said pole portion by a projection beam produced by a double projector.

The second beam produced by said double projector extends in opposite direction to the first one and impinges upon a visual field chart where it plots a marking.

Both beams have a common axis.

The visual field chart is mounted upon a carrier means which is displaceable in its plane by respective means.

The double projector is displaceable in two directions substantially at right angles to each other and to said first and second beam of projection.

Alternatively, it is feasible to tilt the double projector about a centrally arranged universal joint.

Thus it is feasible continuously to displace the fixed point over the entire range of the semi-spheric perimeter screen and, hence, the marking as a reverse projection produces corresponding projections upon the visual field chart in the rear of the perimeter at a spaced relation.

Alternatively, the fixed point projection can be displaced over the screen by coupled hole apertures arranged in the first and second beam of projection, respectively.

Furthermore, discrete test markings are arranged around the central pole portions which can be selectively operated and are realised by the light exit faces of light cables in the plane of the perimeter screen.

A filter is provided in the second projection beam for absorbing the red and infrared spectral range radiation and for transmitting the light from the blue and green spectral range.

Thus it is feasible to continuously observe the position of the marking and, hence, of the actual visual field angle.

Said filter is tiltable so that, when a marking needs recording on the visual field chart.

The filter is switched out of the second beam by operating a push button. Advantageously the visual field chart is a thermo-reactive paper.

A second projector is coupled to said carrier means for illuminating via a hole aperture the light entrance faces of said light cables arranged in one plane.

Thus any desired test marking is illuminated by displacing said carrier means in its plane.

Arrest means are provided to arrest the carrier and thus the second projector in any of the discrete test marking positions. The displacement of the carrier means also displaces the visual field chart relative to the marking and the latter indicates the corresponding position of the illuminated test marking on the visual field chart.

The visual field range defined by the angle between the fixed point, a patient's eye and the test marking can thus be continuously detected between the discrete test markings by displacing the fixed point over the range of the projection screen.

To examine central scotomata a multi-hole aperture can be inserted into the second projector which permits the simultaneous illumination of two or a plurality of test marking symmetrically arranged to the pole portion of said perimeter screen.

The patient fixes in such a manner that the offered test markings are symmetrically positioned in his visual field. With this mode of examination the movable fixed point is used as test marking which is displaced from the pole to the scotoma limit until detected by the patient.

The points thus detected are plotted as described hereinbefore.

Figure 2:
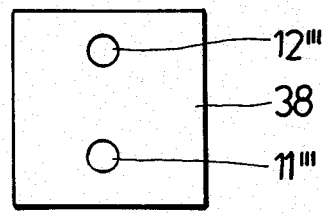

In order that the invention may be more readily understood reference is made to the accompanying drawings which illustrate diagrammatically and by way of example one embodiment thereof and where FIG. 1 is a schematic view of a perimeter system and FIG. 2 an aperture arrangement for a central scotoma examination.

In FIG. 1 a semi-spherical or bowl perimeter screen 3 has a central pole portion 1 which is a flat-white transparent projection screen. In opposition to the rear of the perimeter screen 3 a mount 4 is arranged displaceable in its plane along displacing rods 44, 45 guided by mounting pieces 43, and along directions indicated by arrows 41 and 42.

A visual field chart 5 constituted of thermo-reactive paper is attached to the front face of the mount 4.

An arrest 32 permits to maintain the mount 4 in a desired displaced position.

A double projector 2 is located between the perimeter screen 3 and the visual field chart 5 and is constituted of a light source 19, a first optical system comprising two lenses 22, 20, and inbetween hole aperture 21, and a second optical system comprising two lenses 23, 25 and an inbetween hole aperture 24.

Both, the first and the second optical system are aligned about a common optical axis X—X.

The light source 19 produces a first projection beam $L_1$ and a second projection beam $L_2$ along the optical axis X—X to produce a fixed point 6 for a patient's eye 7 upon the pole portion 1 and a marking 6' which is optically conjugate to the fixed point 6 upon the visual field chart 5.

The central pole portion 1 is substantially symmetrical to the fixed point 6 in the position indicated in FIG. 1. A light stop 35 is switchably arranged in the light beam $L_1$ between the screen 3 and the projector 2. The light stop is switchable by an operation means 36 connected to the light stop 35 via means 36'. A filter 30 transmissive with respect to blue and green radiation only is provided in the light beam $L_2$.

The filter 30 is inserted into or switched out of the light beam by a push button 31 operating, for example, lever means 31'. The double projector 2 is connected to an operating means 18 and 37 which displaces said double projector 2.

The operating means 18 are, for example, lever means, and the operating means 37 a servo-motor. In this embodiment the double projector 2 is tiltable about a joint 46 which has its joint center about the light source 19. It is also feasible to displace the projector 2 or the apertures 21, 22 together in a plane, which is substantially at right angles to the axis X—X.

When the mount 4 is displaced the marking 6' impinges upon other points on the chart 5, for example, upon a point 9', 10', 11', 12', 13', 14'.

A bundle of light cables 8 have their light exit faces in the interiour face of the perimeter screen 3 where they embody discrete test markings, for example 9, 10, 11, 12, 13, 14.

The light entrance faces of the respective light cables 8 are arranged in a plane 15 optically conjugate to the light exit faces so that 9 corresponds to 9'', 10 to 10'', 11 to 11'', 12 to 12'', 13 to 13'' and 14 to 14''. A projector 16 mechanically coupled to the mount 4 and constituted of a light source 26, a condenser lens 27, a hole aperture 28, a light stop 33 and an objective 29 produces a light spot 17 the cross-section of which corresponds to the size of any of the light-cable 8 entrance faces 9'' to 14'' in the plane 15.

The light stop 33 is connected to an operating means 34 to switch the light stop 33 into or out of a light beam $L_3$ originating from the light source 26.

In operation a patient's eye 7 is offered the fixed marking 6 by removing the light stop 35 via operation means 36 out of the light beam $L_1$ originating from the double projector 2 so that said fixed marking 6 is produced in the center 1 of the perimeter screen 3.

The rear projection from the double projector 2 produces a marking 6' optically conjugate to the fixed marking 6 upon the visual field chart 5. In this starting or rest position the marking 6' lies in the center of the chart 5.

This position further means that the light spot 6'' produced by the projector 16 connected to the mount 4 does not impinge on any of the light cable 8 light entrance faces 9'' to 14'' in the plane 15. The marking 6' does not activate the thermo-reactive paper on the chart 5 since the filter 30 is inserted in the beam $L_2$ so that only the green and blue light from the light beam $L_2$ may proceed. When the carrier 4 is displaced with the filter 30 inserted the marking 6' impinges, for example, upon a point 10' the likewise displaced projector 16 illuminates the light entrance face 10'' of the light cables 8 after the light stop 33 has been removed by operation of the operation means 34. In consequence thereof the test marking 10 in the perimeter screen 3 is illuminated. When the patient's eye 7 perceives the test marking 10 the patient pushes the button 31 and the filter 30 is removed from the light beam $L_2$ until the thermo-reactive paper is blackened at point 10' by the light of the beam $L_2$.

In the same manner as the marking 10 also the other discrete markings illuminated by the projector 16 via the light cables 8 serve to define the visual field of the eye 7. Said other discrete markings are regularly distributed on the perimeter screen 3 and the designated markings 9 to 14 which are arranged along circles are only a selection. The projector 16 is successively displaced with the carrier 4 and the chart 5 and, when the respective of the discrete markings 9 to 14 is arrived at the patient which fixates the fixed point 6 is ordered to push the button 31 provided that his eye 7 also perceives the respective one of the discrete markings 9 to 14 which is illuminated. When the patient sees the illuminated discrete marking the latter lies within his visual field and by pushing the button 31 the filter 30 is tilted out of the beam $L_2$ and the corresponding point 9' to 14' is recorded on the chart 5.

When the patient's eye 7 does not perceive the respective marking then the button 31 is not operated and the filter 30 is not removed from the beam $L_2$ and, hence, the point is not recorded.

In this manner the visual field 7 is produced on the chart 5.

By tilting the projector 2 about the joint 46, or by displacing the projector 2 and commonly displacing the apertures 21, 24, respectively, at right angles to the optical axis X—X it is feasible to continuously subdivide the comparatively wide space 5 between the discrete markings 9 to 14 and to record further visual field markings 9' to 13'.

To this end the fixed point 6 is displaced to a new position in the pole portion 1. Thus the test marking 10 appears in the above example by a smaller angle in the visual field of the patient than that defined by the pole portion center 1, the patient's eye 7 and the discrete marking 10.

To this purpose the lever mechanism 18 is operated and the double projector 2 is so displaced that the fixed marking 6 is, for example, radially displaced towards the marking 10 upon the screen 3.

In the course of that displacement the angle included by the patient's eye 7, the fixed marking 6 and the test marking is reduced, and this reduction is rendered visible on the visual field chart 5 by a corresponding displacement of the marking 6' towards the point 11'.

When the patient's eye 7 again perceives the displaced test marking, the patient pushes the button 31 so that the filter 30 is removed from the light beam $L_2$ until the respective point is plotted on the thero-reactive paper at a position between 10' and 11'.

By virtue of the inventional arrangement, it is feasible, though discrete test markings are used, to cover any visual field angle in the vicinity of any discrete test marking.

Furthermore, it is feasible continuously to set (and plot) any desired direction of movement of the test marking in the visual field.

In FIG. 2 a multi-hole aperture 38 is shown the use of which permits the examination of central scotomata.

The multi-hole aperture 38 is exchanged for the hole-aperture 28 in the projector 16 of FIG. 1 and has, for example, holes 11''' and 12'''.

The examination of a central scotoma is carried out as follows. The hole aperture 28 of FIG. 1 is replaced by the multi-hole aperture 38. The patient's eye 7 (FIG. 1) is simultaneously offered the two test markings 11 and 12 after the stop 33 has been removed.

The fixed point (6) which under the condition of a probable central scotoma is not perceived in the center of the visual field, is initially blocked by the stop 35 in the light beam $L_1$.

The patient is now ordered to fixate the marks 11 and 12 with his eye 7 so that they appear symmetrically to the center of the visual field.

The marks 11 and 12 have in this case the same effect as the fixed markings in FIG. 1.

Then the stop 35 is removed and the fixed marking 6, which now becomes the test marking, is moved from the center of the pole portion 1 to the border of the same.

When the patient perceives the moving point 6 he pushes the button 31 and the corresponding point in the visual field chart 5 is recorded.

The fixed point 6 mentioned hereinbefore is a point offered the patient's eye to fixate.

Furthermore, the above invention is not restricted to the disclosed embodiment for recording visual field markings. Any other suitable means for recording and/or storing can be employed.

I claim:

1. Arrangement for test mark positioning in spherical perimeters comprising
    a semi-spherical screen having a concave and a convex face,
        said screen having a light-transmissive central rear projection portion,
    a plurality of test markings being arranged on said concave face,
    a light detecting means,
    a substantially plane mounting means,
        said light detecting means being provided on said mounting means in opposition to said convex face,
    a double-projector for producing a first light beam and a second light beam substantially about an optical axis x—x, and directing said first and said second light beam to said central portion and to said light detecting means, respectively,
        said double-projector being arranged between said central portion and said light detecting means,
        said double-projector, said central portion and said light detecting means being in optical alignment,
    first means for moving said double-projector substantially at right angles to said optical axis x—x,
    second means for displacing said plane mounting means in its plane,
    a projector for producing a third light beam secured to said mounting means,
        said third light beam being substantially at right angles relative to said plane of said mounting means,
    an image plane being optically aligned relative to said projector,
        said projector being for directing said third light beam to said image plane, and
    a plurality of a light cables, the number of said light cables corresponding to the number of said test markings,
        each of said light cables having a light entrance face in said image plane, and a light exit face in said test markings,
        said light entrance faces having the same mutual spaced relation as said test markings on said screen.

2. An arrangement for test mark positioning as claimed in claim 1,
    comprising a first shutter, said first shutter, when operated, being for stopping said first light beam,
    third means for operating said first shutter,
    a filter for affecting said second light beam,
    fourth means for moving and removing said filter into and from, respectively, said second light beam,
    a second shutter provided in said projector, said second shutter, when operated, being for stopping said third light beam,
    and fifth means for operating said second shutter.

3. An arrangement as claimed in claim 2, wherein said light detecting means is a thermo-reactive recording paper.

4. Arrangement as claimed in claim 1, wherein said projector includes an exchangeable aperture having at least two openings.

5. Arrangement as claimed in claim 1, wherein said double-projector is seated in a universal joint.

* * * * *